(12) United States Patent
Gerold et al.

(10) Patent No.: US 9,622,780 B2
(45) Date of Patent: *Apr. 18, 2017

(54) ORTHOPEDIC EXTERNAL FIXATION DEVICE

(71) Applicant: Fixx Orthopedics, LLC, Monticello, MN (US)

(72) Inventors: Thomas Gerold, Monticello, MN (US); Marc Egeland, St. Paul, MN (US); Kenneth Noonan, Madison, WI (US)

(73) Assignee: Fixx Orthopedics, LLC, Monticello, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,260

(22) Filed: Feb. 8, 2016

(65) Prior Publication Data

US 2016/0151091 A1    Jun. 2, 2016

Related U.S. Application Data

(63) Continuation of application No. 14/160,668, filed on Jan. 22, 2014, now Pat. No. 9,301,783.
(Continued)

(51) Int. Cl.
*A61B 17/64* (2006.01)

(52) U.S. Cl.
CPC .......... *A61B 17/6416* (2013.01); *A61B 17/64* (2013.01); *A61B 17/6458* (2013.01)

(58) Field of Classification Search
CPC .. A61B 17/6458; A61B 17/64; A61B 17/6416
(Continued)

(56) References Cited

U.S. PATENT DOCUMENTS 2,398,915 A  *  4/1946  Bell ..................... A61B 17/685
                                                                279/44
3,389,734 A     6/1968  Gutshall
(Continued)

FOREIGN PATENT DOCUMENTS

CA       2081466      8/1992
CA       2159295      3/1996
(Continued)

OTHER PUBLICATIONS

International Search Report and Written Opinion mailed in PCT/US16/19486, Jul. 11, 2016.

*Primary Examiner* — Pedro Philogene
*Assistant Examiner* — David C Comstock
(74) *Attorney, Agent, or Firm* — Bell & Manning, LLC

(57) ABSTRACT

Devices for the fixation of a bone fracture and methods of using the devices are provided. The devices comprise at least one distal pin assembly configured to engage a first bone fragment, at least one proximal pin assembly configured to engage a second bone fragment, and a rail bar system configured to connect the distal and proximal pin assemblies together across the bone fracture. Each pin assembly includes a screw portion having a distal end configured to engage first bone fragment and a proximal end, a support sheath portion having a distal end configured to engage the first bone fragment, wherein the support sheath portion defines an elongated channel in which the proximal end of the screw portion is disposed, and a cap portion configured to attach the proximal end of the screw portion to the support sheath portion.

12 Claims, 11 Drawing Sheets

Related U.S. Application Data

(60) Provisional application No. 61/755,618, filed on Jan. 23, 2013.

(58) Field of Classification Search
USPC .............................. 606/54, 59, 264, 265, 266
See application file for complete search history.

(56) References Cited

U.S. PATENT DOCUMENTS

| | | | | |
|---|---|---|---|---|
| 4,620,533 | A * | 11/1986 | Mears | A61B 17/645 606/54 |
| 4,848,368 | A | 7/1989 | Kronner | |
| 4,850,746 | A | 7/1989 | Finsterwalder et al. | |
| 4,920,959 | A | 5/1990 | Witzel et al. | |
| 5,891,144 | A | 4/1999 | Mata et al. | |
| 7,717,919 | B2 * | 5/2010 | Assell | A61B 17/1757 606/247 |
| 9,131,946 | B2 | 9/2015 | Larche et al. | |
| 9,301,783 | B2 * | 4/2016 | Gerold | A61B 17/6458 |
| 2005/0277936 | A1 | 12/2005 | Siravo et al. | |
| 2006/0002784 | A1 | 1/2006 | Curtis | |
| 2008/0300630 | A1 | 12/2008 | Bonnema et al. | |
| 2012/0203225 | A1 | 8/2012 | Mingozzi et al. | |
| 2014/0277129 | A1 | 9/2014 | Arai et al. | |
| 2014/0303621 | A1 | 10/2014 | Gerold et al. | |
| 2014/0364853 | A1 | 12/2014 | Mullaney et al. | |

FOREIGN PATENT DOCUMENTS

| | | |
|---|---|---|
| CA | 2371670 | 8/2002 |
| CA | 2372713 | 8/2002 |
| CA | 2424020 | 9/2003 |
| CN | 204164141 U | 2/2015 |
| DE | 2607315 | 9/1976 |
| EP | 1839584 | 10/2007 |
| ES | 2126497 | 3/1999 |
| FR | 2674120 | 9/1992 |
| FR | 19910003977 | 9/1992 |
| FR | 2783703 | 3/2000 |
| FR | 2968535 | 6/2012 |
| GB | 8809120 | 5/1988 |
| KR | 20070006596 | 1/2007 |
| WO | WO0205718 | 1/2002 |
| WO | WO2008027375 | 3/2008 |
| WO | WO2010121028 | 10/2010 |
| WO | WO2012040862 | 4/2012 |
| WO | WO2013119812 | 8/2013 |
| ZA | 9904846 | 2/2000 |
| ZA | 9904847 | 2/2000 |

* cited by examiner

ORTHOPEDIC EXTERNAL FIXATION DEVICE

CROSS-REFERENCE TO RELATED APPLICATIONS

The present application is a continuation of U.S. patent application Ser. No. 14/160,668 that was filed Jan. 22, 2014, the entire contents of which are hereby incorporated by reference; which claims priority to U.S. Provisional Patent Application No. 61/755,618 that was filed Jan. 23, 2013, the entire contents of which is hereby incorporated by reference.

BACKGROUND

Bone fractures are debilitating injuries that affect millions of people around the world each year. Many of these fractures involve the long bones of the extremities including the femur, tibia, fibula, humerus, radius, and ulna. Fractures to these bones can be particularly painful, difficult to heal, and may require multiple surgeries with months of recovery.

When a patient enters the emergency room with a severe bone fracture, it is often accompanied by many other serious injuries. For instance, bone fractures are a frequent occurrence after a serious car accident, where often times the individual will also have head and respiratory trauma that is of primary concern. Though the critical injuries must be addressed first, once the patient is stable in the emergency department any serious fractures must be stabilized. The patient may need to be transported throughout the emergency department for various imaging and surgical procedures, so it is important to have the injured limb temporarily stabilized to reduce pain and prevent improper healing. Temporary stabilization may be required until the patient and his or her injuries are stable enough for a surgical procedure in the operating room to repair and permanently fixate the fracture. This temporary period can be anywhere from a few hours to a week, depending on the injuries. Once placed, a permanent device may remain affixed for a number of weeks or even months, until the fracture is adequately healed.

There are several forms of temporary fracture stabilization methods including splinting, traction, and external fixation. Splinting may provide support along a fracture until the patient's other critical injuries are stabilized; however, such temporary devices are not always compatible with certain imaging techniques, such as magnetic resonance imaging (MRI), and don't actually fixate the fracture.

Traction is a method for temporary fracture stabilization used in many hospitals and emergency departments. Traction systems separate the two major bone fragments, properly aligning them (reduction) and facilitating proper healing. However, traction is a bulky procedure and can subject the patient to an uncomfortable position without the ability to move for an extended period of time. Bed transfers with this type of fixation are highly impractical, and very difficult to orchestrate.

External fixators have been used for over a century and have two widespread uses: temporary fixation and more permanent applications intended for a longer term treatment (permanent external fixation). Methods for permanent external fixation may utilize multi-pin circular frames and unilateral pin-bar systems. Though effective in stabilizing the fracture and keeping the fragments aligned for healing, the installation of these permanent fixation devices can takes hours, and the complexity involved with unilateral and pin-point bone screw affixation can be complicated.

Temporary fixation involves the rapid temporary fixation of bone fractures using primarily unilateral pin-bar fixators to provide temporary stability while the patient is stabilized and care is provided during hospitalization. Current temporary fixators employ, at a minimum, four separate pins to achieve fixation. Such devices can take critical time to be applied and pose an increased risk for infection at the exposed sites of pin entry.

SUMMARY

Devices for the temporary or permanent fixation of bone fractures are provided. Also provided are methods of using the devices for the fixation of bone fragments. The device comprises at least one distal pin assembly configured to engage a first bone fragment, at least one proximal pin assembly configured to engage a second bone fragment, wherein the second bone fragment is at least partially separated from the first bone fragment by a bone fracture, and a rail bar system configured to connect the distal and proximal pin assemblies together across the bone fracture.

In one embodiment, the distal pin assembly includes a screw portion having a distal end configured to engage a first bone fragment and a proximal end, a support sheath portion having a distal end configured to engage the first bone fragment, wherein the support sheath portion defines an elongated channel in which the proximal end of the screw portion is disposed, and a cap portion attaching the proximal end of the screw portion to the support sheath portion. The proximal pin assembly comprises a screw portion having a distal end configured to engage a second bone fragment and a proximal end, a support sheath portion having a distal end configured to engage the second bone fragment, wherein the support sheath portion defines an elongated channel in which the proximal end of the screw portion is disposed, and a cap portion attaching the proximal end of the screw portion to the support sheath portion. The rail bar system can comprise one or more rigid support structures configured to connect the cap portion of the distal pin assembly to the cap portion of the proximal pin assembly.

In another embodiment, the distal pin assembly includes a screw portion, the screw portion having a distal end configured to engage a first bone fragment and a proximal end, and a cap portion attached to the proximal end of the screw portion. The proximal pin assembly comprises a screw portion having a distal end configured to engage a second bone fragment and a proximal end and a cap portion attached to the proximal end of the screw portion. The rail bar system can comprise one or more rigid support structures configured to connect the cap portion of the distal pin assembly to the cap portion of the proximal pin assembly.

In some embodiments, the distal pin assembly comprises a cap portion comprising a hemispherical surface configured to engage with the rail bar system to connect the distal pin assembly to the rail bar system and a proximal pin assembly having a cap portion comprising a hemispherical surface configured to engage with the rail bar system to connect said proximal pin assembly to the rail bar system.

In some embodiments, the distal end of said support sheath portion of the distal pin assembly comprises tines configured to engage the first bone fragment and the distal end of the support sheath portion of said proximal pin assembly comprises tines configured to engage the second bone fragment.

In some embodiments, the distal end of the screw portion of the distal pin assembly comprises forward threaded screw threads and the distal end of the screw portion of the proximal pin assembly comprises reverse threaded screw threads. Such a design allows the device to self-lock against both motion and rotation once inserted into the bone fragments. For example, if the fracture fragments are stressed during movement (i.e., a limb may be lifted during patient transport, so the only force applied would be in the vertical direction) the screw threading counteracts the torque experienced during such a lift.

In some embodiments, the distal end of the screw portion of the distal pin assembly comprises a self-boring and self-tapping tip adjacent to a section of cylindrical threading which transitions into a section of conical threading and the distal end of the screw portion of the proximal pin assembly comprises a self-boring and self-tapping tip adjacent to a section of cylindrical threading which transitions into a section of conical threading. Such a design allows the device to self-lock against both motion and rotation and prevents the screw portions of each pin assembly from backing out of their holes within the respective bone fragments during movement of the bone fracture.

In some embodiments, the device comprises only two pin assemblies.

One embodiment of a method of treating a bone fracture with the present devices comprises engaging a first bone fragment with at least one distal pin assembly and engaging a second bone fragment with at least one proximal pin assembly. The distal and proximal pin assemblies are then connected using the rail bar system.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

The following description of the embodiments of the devices and methods is merely illustrative and is not intended to limit the invention to a specific embodiment or its use to a specific application.

Figure 1:
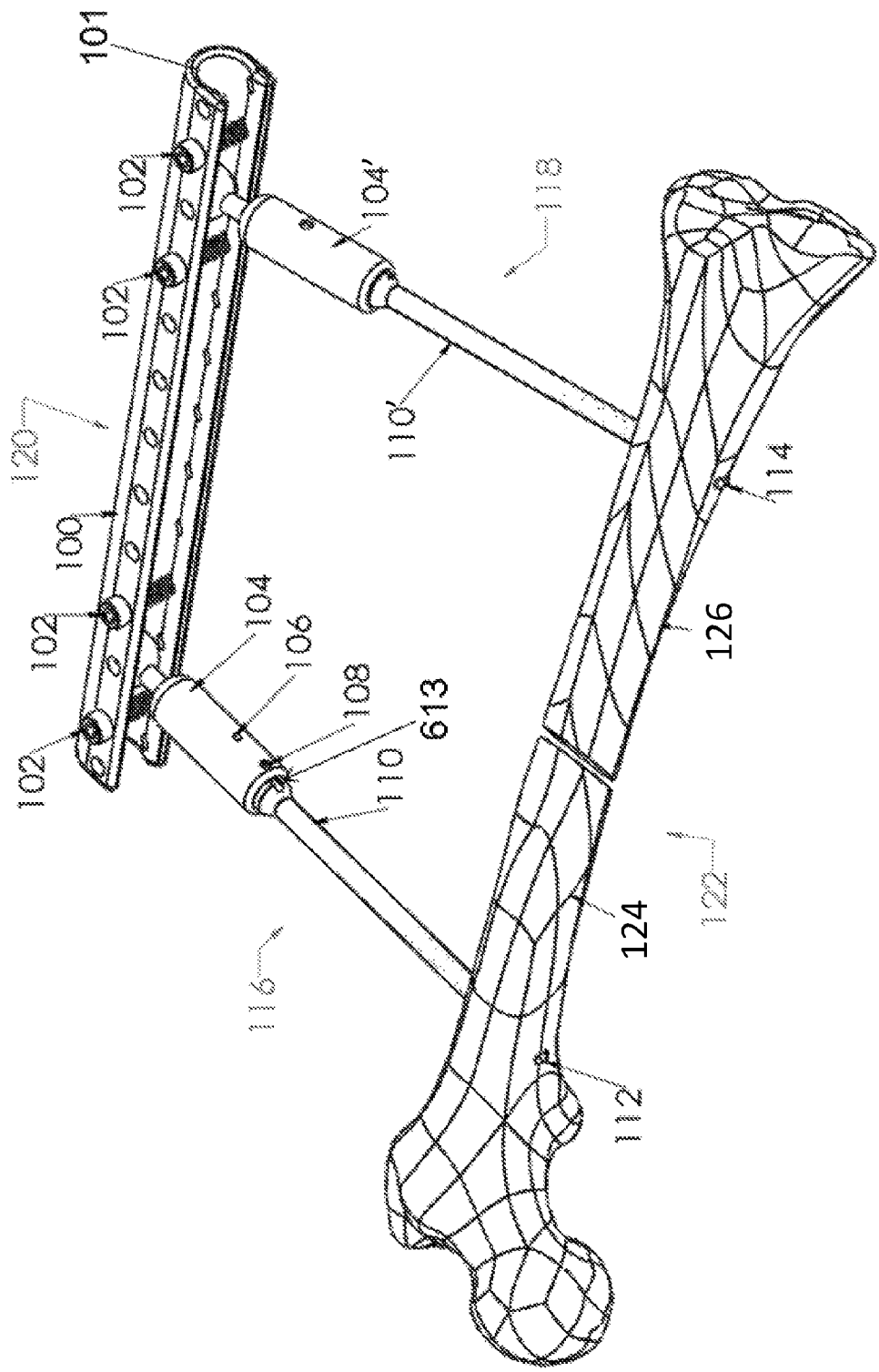
FIG. 1 shows a perspective view of an embodiment of an external fixation device fixated to a fractured bone.
Figure 2:
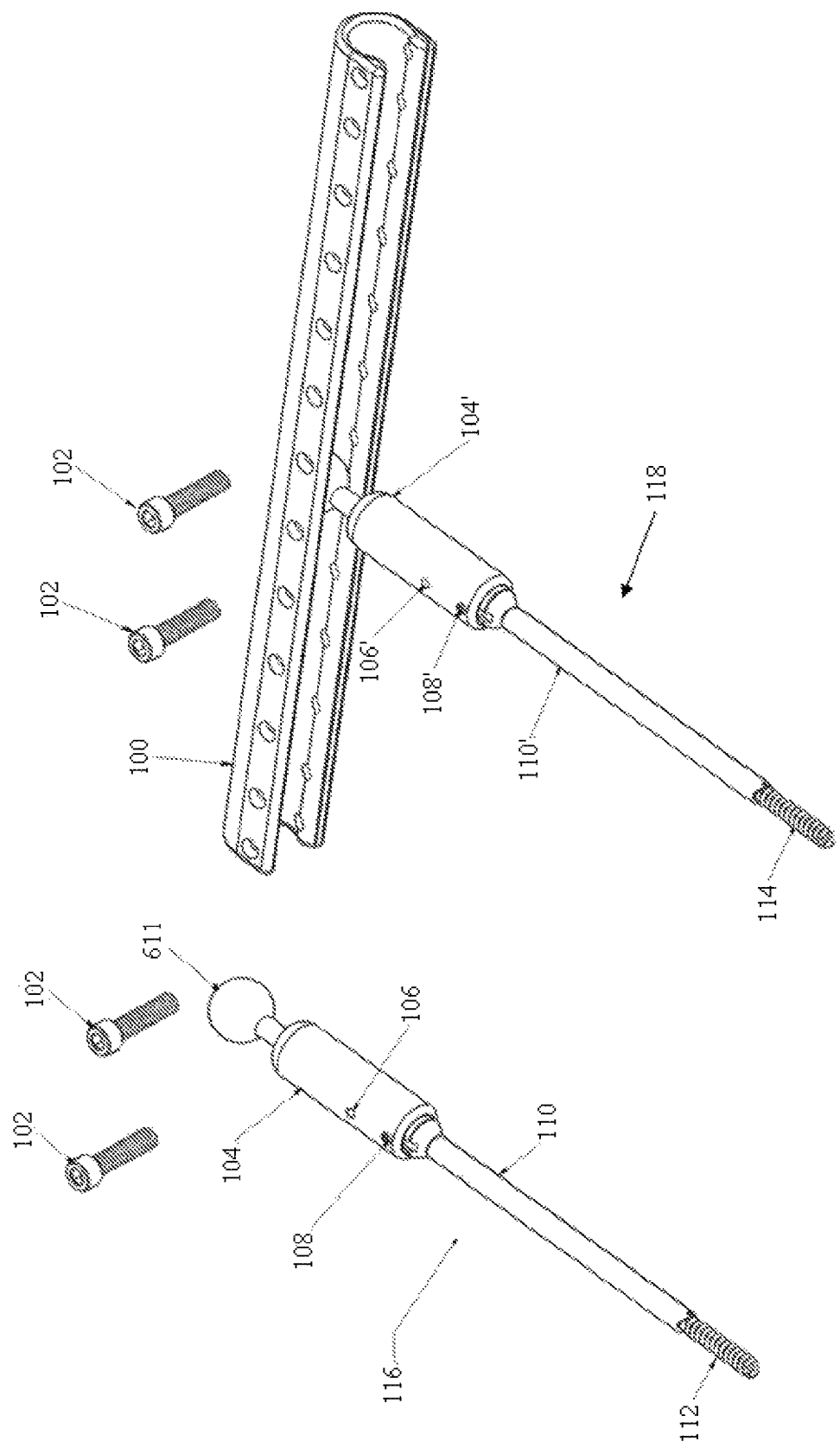
FIG. 2 shows an exploded perspective view of an embodiment of an external fixation device.
Figure 3:
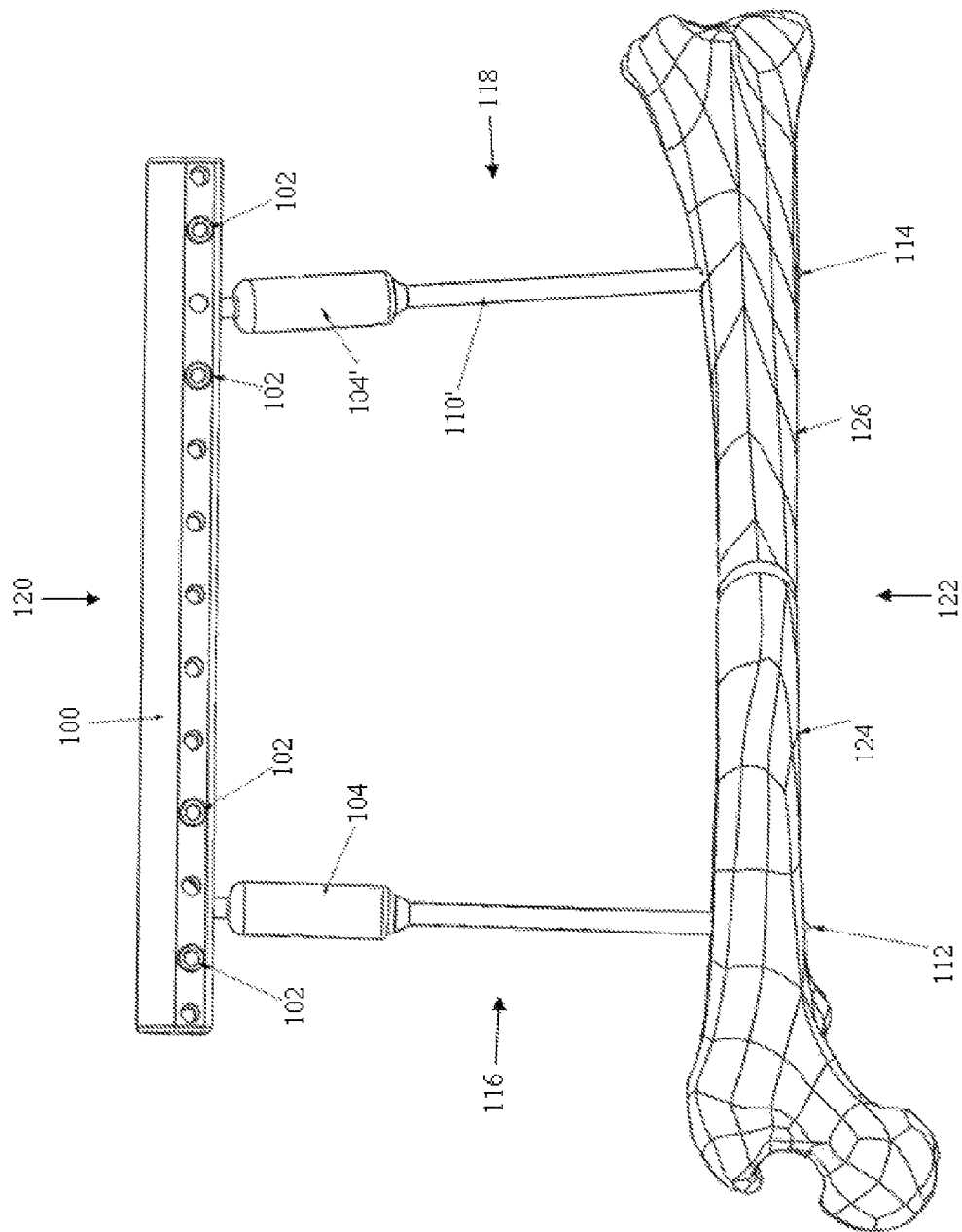
FIG. 3 shows a front view of an embodiment of an external fixation device fixated to a fractured bone.
Figure 4:
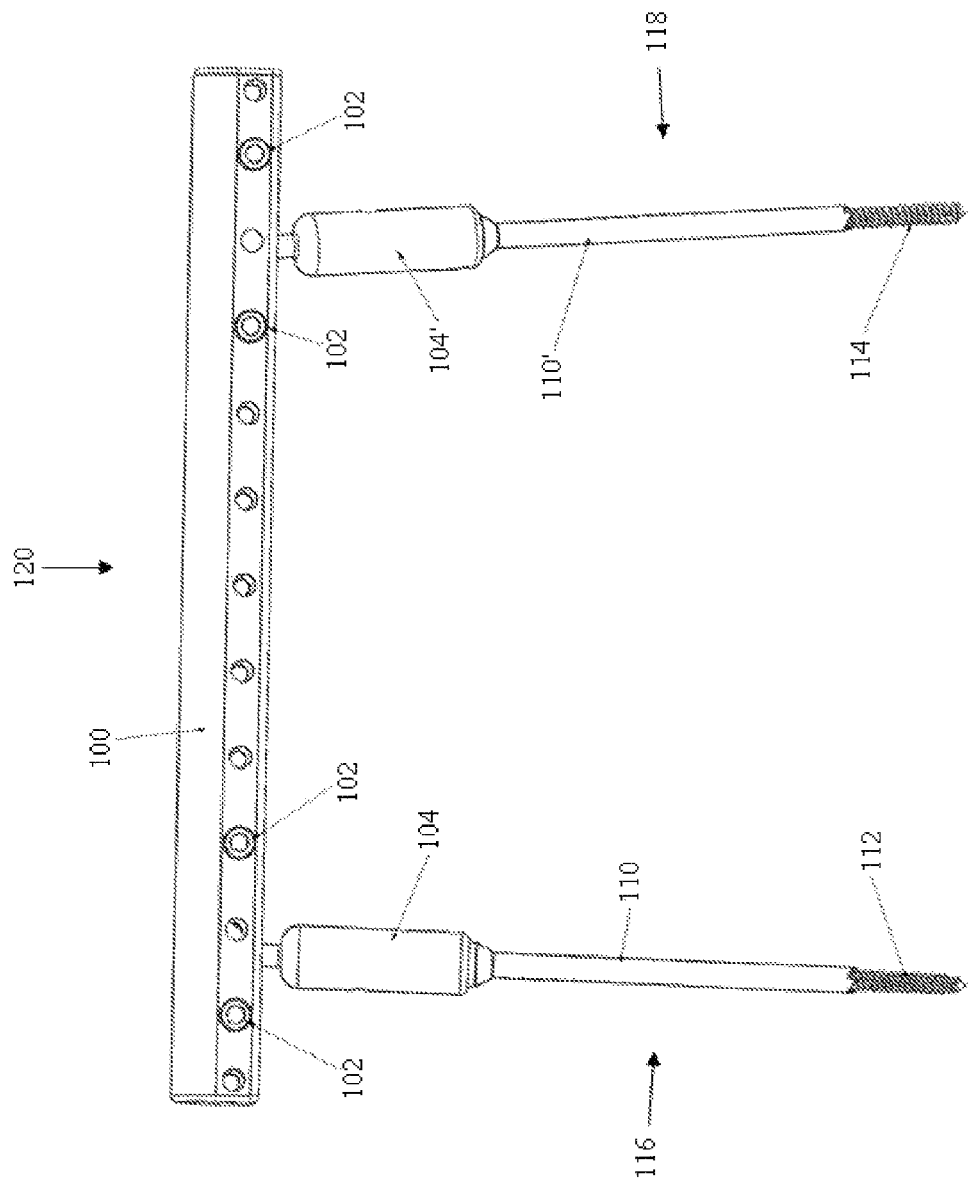
FIG. 4 shows a front view of an embodiment of an external fixation device.
Figure 5:
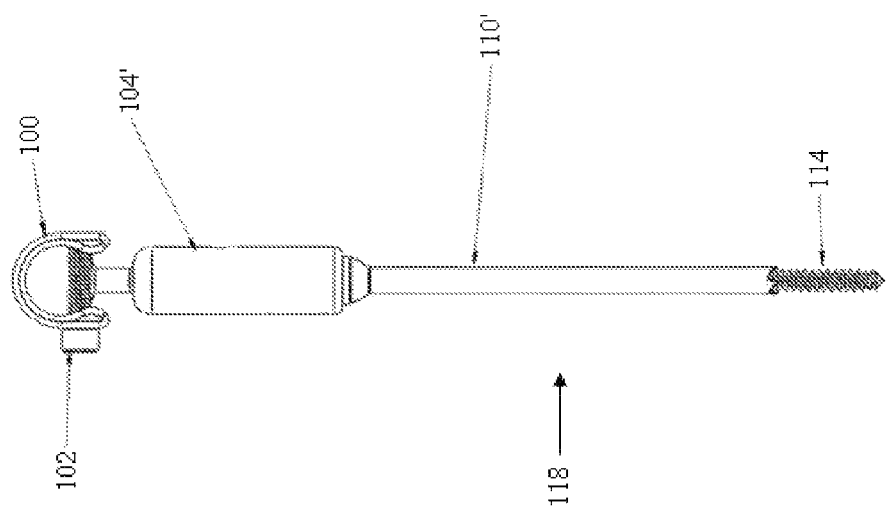
FIG. 5 shows a side view of an embodiment of an external fixation device.

One embodiment of an orthopedic external fixation device 120 is shown in FIG. 1, FIG. 3, and FIG. 4. FIG. 4 shows orthopedic external fixation device 120 alone. FIG. 1 and FIG. 3 show orthopedic external fixation device 120 in combination with fractured bone 122. The orthopedic external fixation device 120 includes distal pin assembly 116 configured to screw into first bone fragment 124; proximal pin assembly 118 configured to screw into second bone fragment 126; and rail bar system 100 configured to connect distal pin assembly 116 to proximal pin assembly 118. Distal pin assembly 116 comprises screw cap 104 configured to connect distal pin assembly 116 to rail bar system 100; support sheath portion 110 configured to engage first bone fragment 124; and a screw portion 112 having a distal end configured to screw into first bone fragment 124 and a proximal end. Proximal pin assembly 118 comprises screw cap 104' configured to connect proximal pin assembly 118 to rail bar system 100; support sheath 110' configured to engage second bone fragment 126; and a screw portion 114 having a distal end configured to screw into second bone fragment 126 and a proximal end.

The terms "distal end" and "proximal end" are used throughout this disclosure in reference to the screw portion, the support shealth portion and the cap screw cap of each pin assembly. As used herein the "distal end" refers to the end of the component that is nearest the bone fragment when the pin assembly is in place and the "proximal end" refers to the end of the component that is disposed opposite, or substantially opposite, the distal end.

As shown in this embodiment, each support sheath portion has a distal end configured to engage a bone fragment, wherein the support sheath portion defines an elongated channel in which the proximal end of a screw portion is disposed and out of which the distal end of the screw portion extends. For example, the support sheath portion may comprise a distal end, an oppositely disposed proximal end and a body (e.g., a hollow shaft) connecting the distal and proximal ends, wherein the elongated channel extends through the body from the distal end to the proximal end. The engagement between a bone fragment and the distal end of the support sheath portion may be provided, for example, by extensions (e.g., tines) at the distal end of the sheath that are configured to anchor the sheath portion to a bone fragment and hold the sheath portion in a given position along the bone fragment. The support sheath portion fits over the screw portion to allow the support sheath portion to slide over the proximal end of the screw portion and engage the bone fragment.

Figure 6:
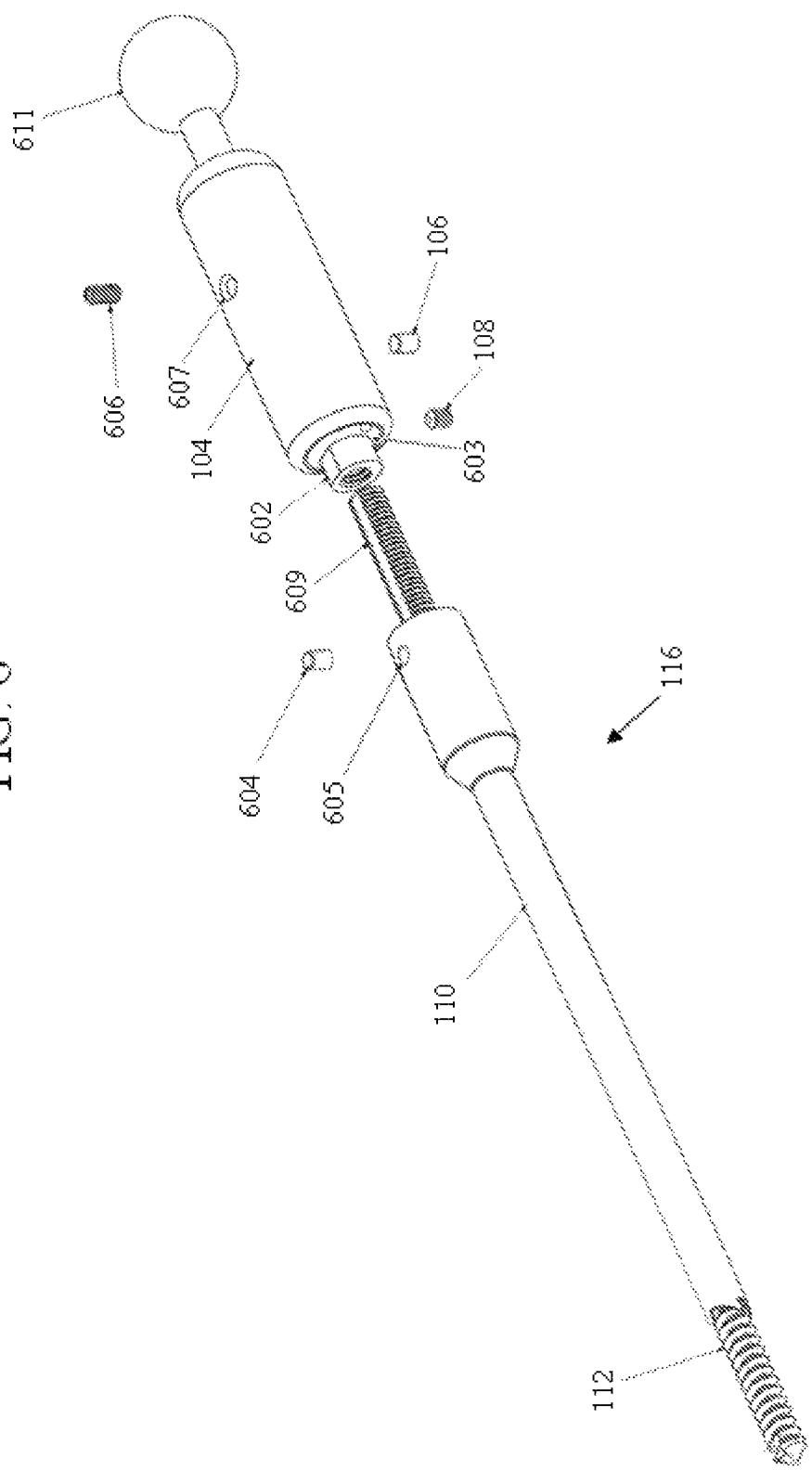
FIG. 6 shows an exploded perspective view of an embodiment of a pin assembly for an external fixation device.

In the present embodiment, as best seen in FIG. 6, support sheath portion 110 of distal pin assembly 116 slides over screw portion 112, such that the distal end of screw portion 112 extends out of the distal end of support sheath portion 110. In the embodiment depicted in this figure, the proximal end of support sheath portion 110 is wider than its distal end and is configured to engage with the distal end of screw cap 104.

The distal end of screw cap 104 defines a bore hole the inner surface of which comprises internal screw threads (e.g., a nut) 602 configured to engage with the threaded proximal end of screw portion 112 and to determine the length of screw portion 112 that enters into the interior volume of screw cap 104. The distal end of screw cap 104 further defines an opening 603 configured to receive the proximal end of support sheath portion 110. Screw cap 104 further comprises a proximal end disposed opposite its distal end and a body, such as a hollow shaft, extending between the proximal and distal ends. In the embodiment of FIG. 6, the proximal end of screw cap 104 comprises an extension that forms a hemispherical surface 611.

Once the proximal end of support sheath portion 110 has been inserted into the distal end of screw cap 104, lower screw cap portion thumbscrew 108 can be tightened against support sheath portion 110 to hold it in place. Similarly, once the proximal end of screw portion 112 has been inserted to screw cap 104, upper screw cap portion thumbscrew 606 can be tightened against screw portion 112 to hold it in place. A support sheath portion plug 604, configured to be inserted through hole 605 in the wall of support sheath portion 110 and to ride along a flat section 609 running along at least a portion of the length of the outer surface of screw portion 112, can be used to ensure proper alignment of distal pin assembly 116. Similarly, a screw cap plug 106, configured to ride in a channel 613 (visible in FIG. 1) present on the proximal end of support sheath portion 110, can be used to ensure proper alignment of distal pin assembly 116. The proximal pin assembly 118 has the same overall organization as shown here for distal pin assembly 116.

Figure 7:
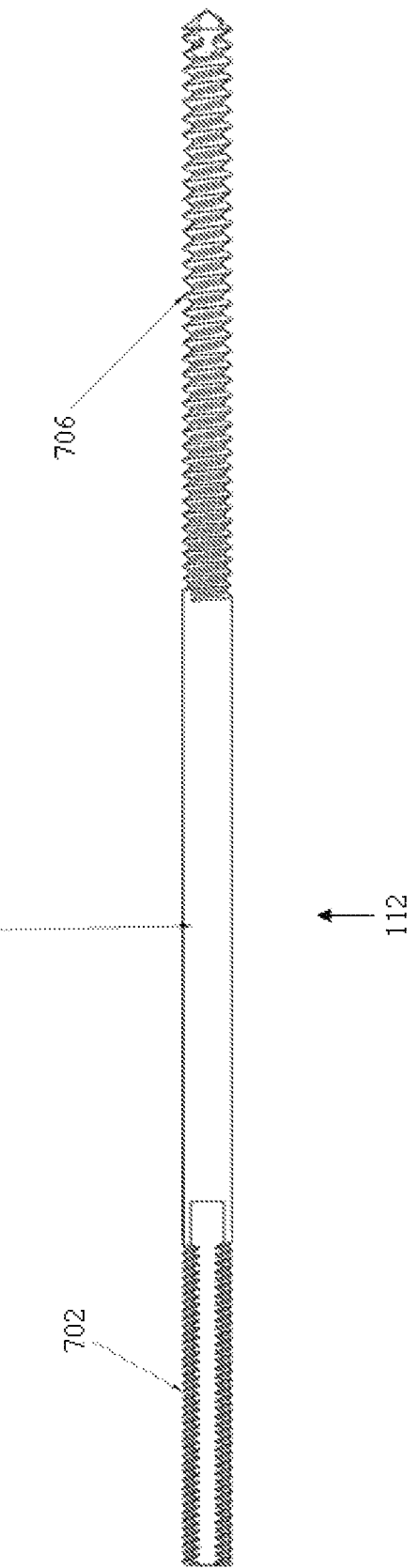
FIG. 7 shows a front view of an embodiment of a screw portion of a pin assembly for an external fixation device.

FIG. 7 shows only screw portion 112. Screw portion 112 has a distal end 706 configured to screw into a first bone fragment, a proximal end 702 comprising threads to engage threaded bore hole 602, and an unthreaded shaft 704 extending between distal end 706 and proximal end 702.

Figure 8:
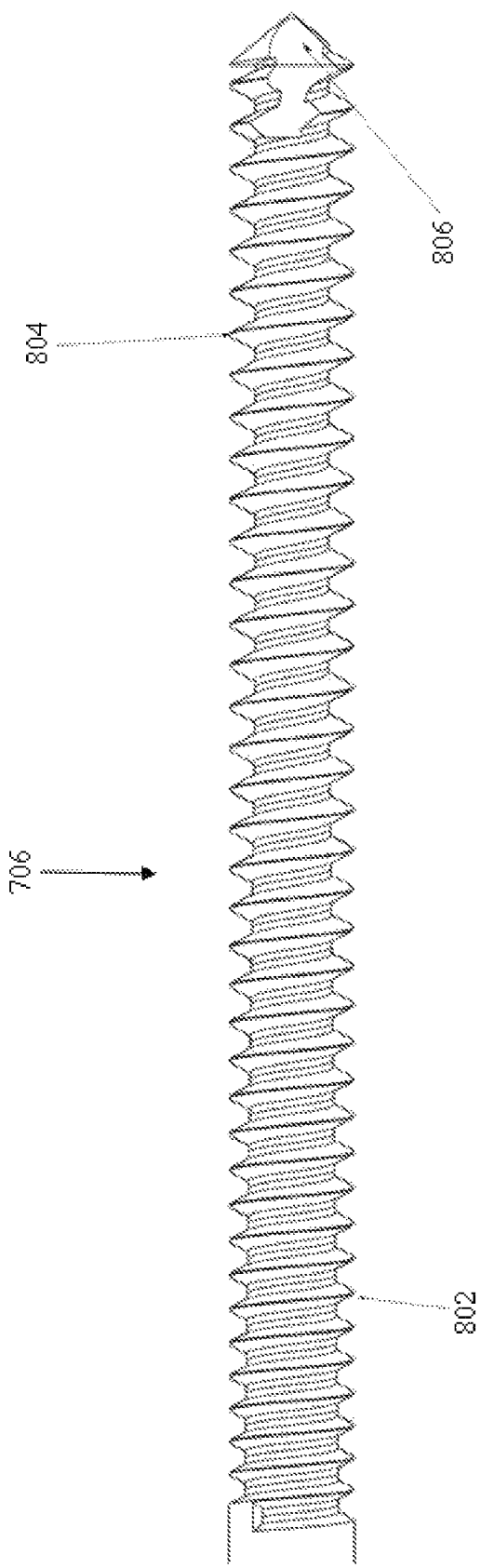
FIG. 8 shows a front view of an embodiment of a screw portion of a pin assembly for an external fixation device having a self-boring and self-tapping tip adjacent to a section of cylindrical threading which transitions into a section of conical threading.

As seen in FIG. 8, distal end 706 of screw portion 112 optionally comprises a self-boring and self-tapping screw tip 806 adjacent to a section of cylindrical threads 804 that transitions into a section of conical threads 802.

As shown in FIGS. 1-5, rail bar system 100 optionally is configured to connect to screw cap 104 of distal pin assembly 116 and screw cap 104' of proximal pin assembly 118. As shown here, the two pin assemblies can be spaced apart along the rail bar system, such that the rail bar system forms a bridge between the pin assemblies. The rail bar system is desirably designed such that the spacing between the two pin assemblies can be adjusted. For example, rail bar system 100 defines a groove 101 configured to slidably engage with hemispherical surfaces on screw caps 104 and 104'. The position of the hemispherical surface of each screw cap 104 and 104' in the groove can be adjusted to a desired location and that location can be fixed by tightening cap screws 102 on either side of each hemispherical surface.

Figure 9:
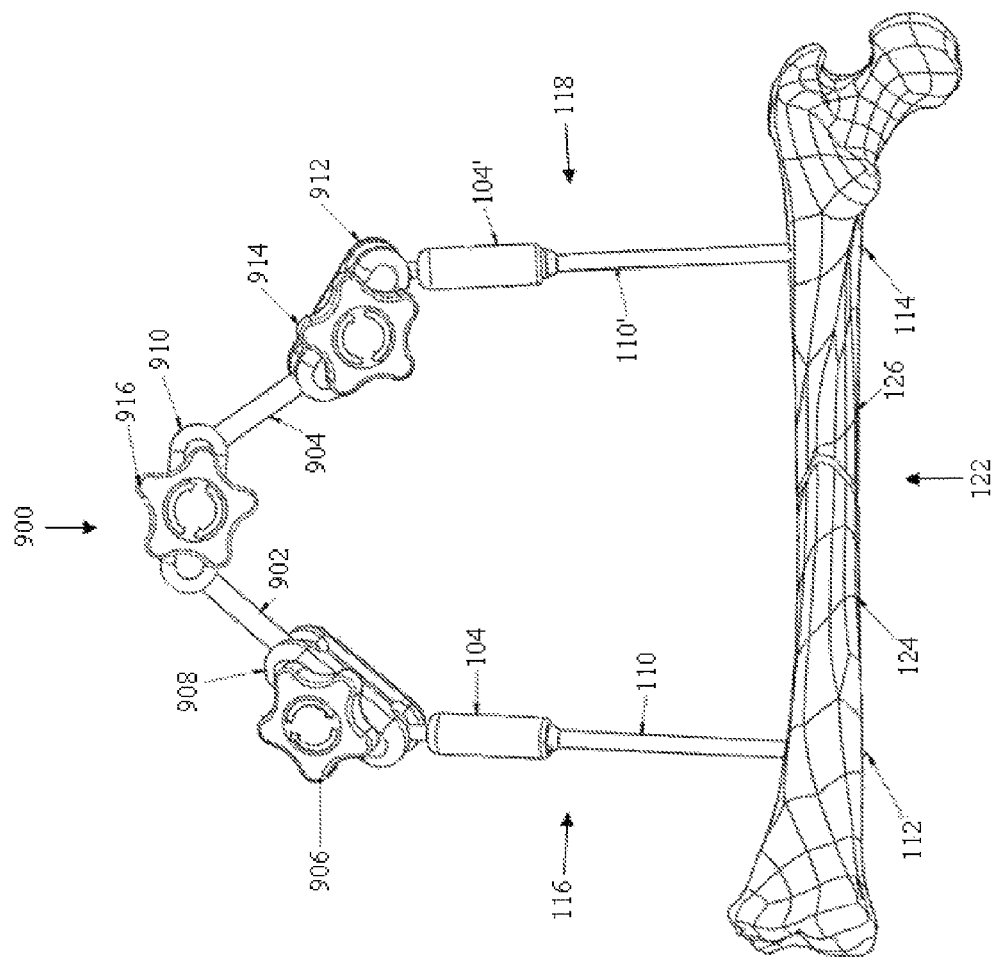
FIG. 9 shows a front view of an embodiment of an external fixation device fixated to a fractured bone.
Figure 10:
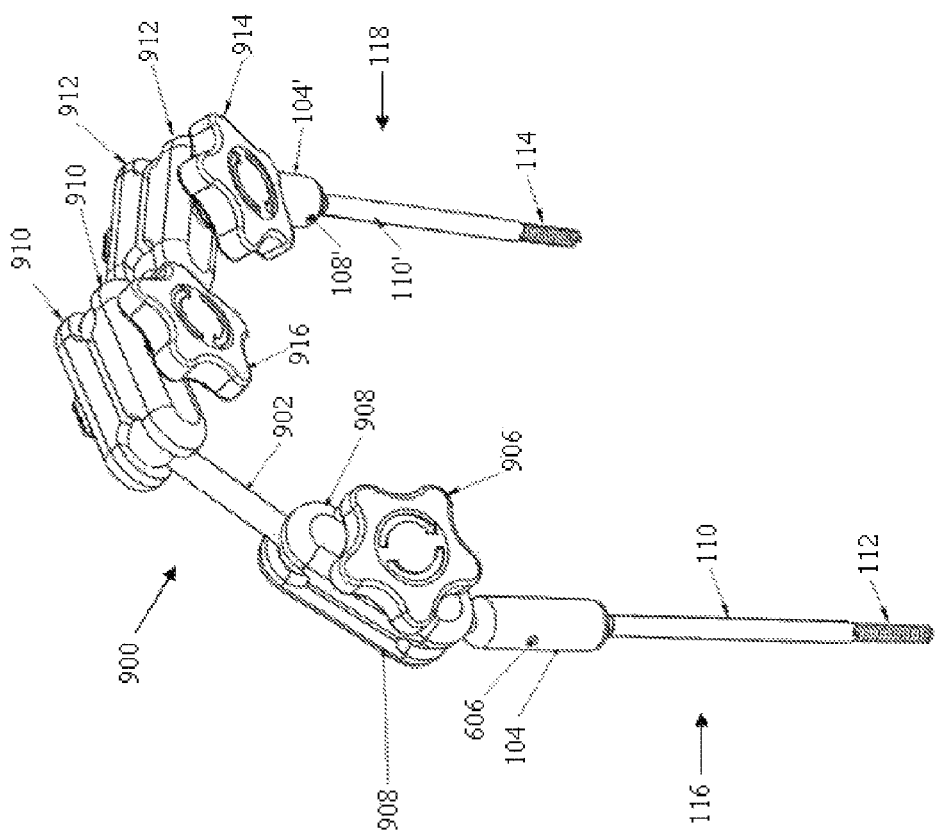
FIG. 10 shows a perspective view of an embodiment of an external fixation device.
Figure 11:
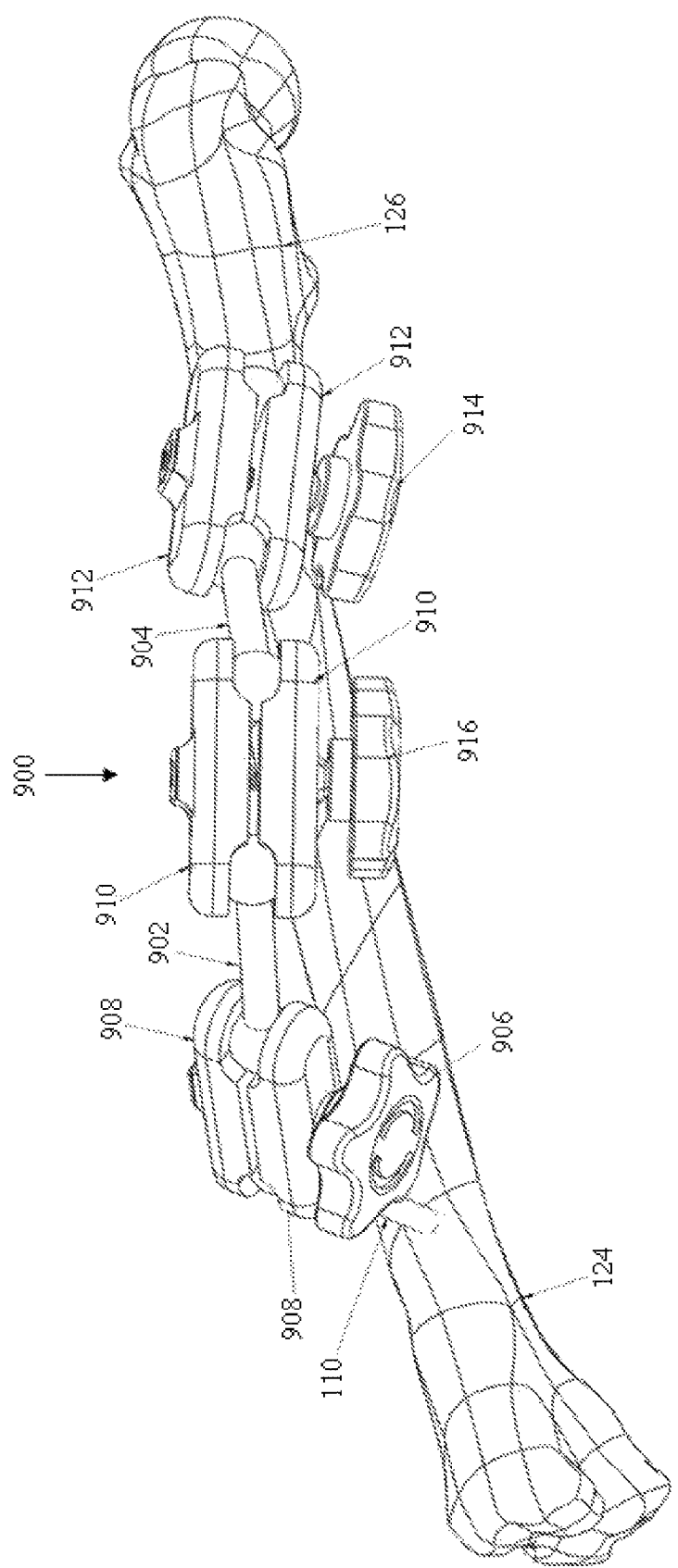
FIG. 11 shows a top view of an embodiment of an external fixation device.

Another embodiment of a rail bar system is shown in FIGS. 9-11. In embodiments such as this, the spacing between the pin assemblies can be made adjustable by including one or more adjustable joints along the rail bar system. As seen in FIGS. 9-11, the joints of rail bar system 900 may comprise ball joints comprising one or more ball connectors and socket connectors. As seen by the configuration shown in FIGS. 9-11, two socket connectors 908 connect screw cap 104 of distal pin assembly 116 to one end of a first ball connector 902. The ball and socket joint formed by two socket connectors 908 and screw cap 104 or two socket connectors 908 and ball connector 902 can be tightened using knob screw 906. Likewise, two socket connectors 912 connect screw cap 104' of proximal pin assembly 118 to a second ball connector 904. Such ball and socket joints, can also be tightened using a second knob screw 914. The free ends of both ball connectors 902 and 904 are joined by a third set of two socket connectors 910 and can also be tightened using a third knob screw 916.

In another embodiment, the orthopedic external fixation device of the present invention includes distal pin assembly 116 configured to screw into a first bone fragment; proximal pin assembly 118 configured to screw into a second bone fragment; and rail bar system 100 configured to connect distal pin assembly 116 to proximal pin assembly 118. Distal pin assembly 116 comprises screw cap 104 configured to connect distal pin assembly 116 to rail bar system 100 or 900 and distal pin screw 112 configured to screw into first bone fragment. Proximal pin assembly 118 comprises screw cap 104' configured to connect proximal pin assembly 118 to rail bar system 100 or 900 and proximal pin screw 114 configured to screw into second bone fragment. Rail bar system 100 or 900 is configured to connect to screw cap 104 of distal pin assembly 116 to screw cap 104' of proximal pin assembly 118.

While various descriptions of the present invention are described above, it should be understood that the various features can be used singly or in any combination. Therefore, the present invention is not limited to only the specific embodiments depicted herein.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A device for fixation of a bone fracture comprising:
   a. at least one distal pin assembly configured to engage a first bone fragment, said distal pin assembly comprising (i) a screw portion having a distal end configured to engage the first bone fragment and a proximal end, (ii) a support sheath portion having a distal end configured to engage the first bone fragment, wherein the support sheath portion defines an elongated channel in which the proximal end of the screw portion is disposed, and (iii) a cap portion connecting said proximal end of said screw portion to said support sheath portion; and
   b. at least one proximal pin assembly configured to engage a second bone fragment, said proximal pin assembly comprising (i) a screw portion having a distal end configured to engage the second bone fragment and a proximal end, (ii) a support sheath portion having a distal end configured to engage the second bone fragment, wherein the support sheath portion defines an elongated channel in which the proximal end of the screw portion is disposed, and (iii) a cap portion connecting said proximal end of said screw portion to said support sheath portion;
   wherein said distal pin assembly is connected to said proximal pin assembly.

2. The device of claim 1, wherein the distal end of said support sheath portion of said distal pin assembly comprises tines configured to engage said first bone fragment and the distal end of said support sheath portion of said proximal pin assembly comprises tines configured to engage said second bone fragment.

3. The device of claim 2, wherein the proximal end of the support sheath portion of the distal pin assembly is engaged with a distal end of the cap portion of the distal pin assembly; and the proximal end of the support sheath portion of the proximal pin assembly is engaged with a distal end of the cap portion of the proximal pin assembly.

4. The device of claim 3, wherein said distal pin assembly is connected to said proximal pin assembly by one or more ball and socket joints.

5. The device of claim 2, wherein said distal pin assembly is connected to said proximal pin assembly by one or more ball and socket joints.

6. The device of claim 1, wherein the proximal end of the screw portion of the distal pin assembly comprises threads that are engaged with a threaded bore hole in the cap portion of the distal pin assembly; and the proximal end of the screw portion of the proximal pin assembly comprises threads that are engaged with a threaded bore hole in the cap portion of the proximal pin assembly.

7. The device of claim 6, wherein said distal pin assembly is connected to said proximal pin assembly by one or more ball and socket joints.

8. The device of claim 1, wherein said distal pin assembly is connected to said proximal pin assembly by one or more ball and socket joints.

9. A method of using the device in claim 1 to stabilize a fractured bone comprising a first bone fragment and a second bone fragment, the method comprising:
  a. engaging the first bone fragment with the distal end of the screw portion of the distal pin assembly;
  b. engaging the first bone fragment with the distal end of the support sheath portion of the distal pin assembly;
  c. engaging the second bone fragment with the distal end of the screw portion of the proximal pin assembly;
  d. engaging the second bone fragment with the distal end of the support sheath portion of the proximal pin assembly; and
  e. connecting said distal pin assembly to said proximal pin assembly.

10. The method of claim 9, wherein engaging the first bone fragment with the distal end of the screw portion of the distal pin assembly comprises screwing the distal end of the screw portion of the distal pin assembly into the first bone fragment; and engaging the second bone fragment with the distal end of the screw portion of the proximal pin assembly comprises screwing the distal end of the screw portion of the proximal pin assembly into the second bone fragment.

11. The method of claim 10, wherein the distal end of said support sheath portion of said distal pin assembly comprises tines and the distal end of said support sheath portion of said proximal pin assembly comprises tines; and further wherein engaging the first bone fragment with the distal end of the support sheath portion of the distal pin assembly comprises engaging the tines of said support sheath portion of said distal pin assembly with the first bone fragment; and engaging the second bone fragment with the distal end of the support sheath portion of the proximal pin assembly comprises engaging the tines of said support sheath portion of said proximal pin assembly with the second bone fragment.

12. The method of claim 9, wherein the proximal end of the screw portion of the distal pin assembly comprises threads that are configured to engage with a threaded bore hole in the cap portion of the distal pin assembly; and the proximal end of the screw portion of the proximal pin assembly comprises threads that are configured to engage with a threaded bore hole in the cap portion of the proximal pin assembly; the method further comprising: engaging the threads of the proximal end of the screw portion of the distal pin assembly with the threaded bore hole in the cap portion of the distal pin assembly; and engaging the threads of the proximal end of the screw portion of the proximal pin assembly with the threaded bore hole in the cap portion of the proximal pin assembly.

* * * * *